(12) United States Patent
Valoir

(10) Patent No.: US 9,968,422 B2
(45) Date of Patent: May 15, 2018

(54) SHAPEABLE BITE PLATES

(71) Applicant: OrthoAccel Technologies, Inc., Bellaire, TX (US)

(72) Inventor: Tamsen Valoir, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 707 days.

(21) Appl. No.: 14/031,832

(22) Filed: Sep. 19, 2013

(65) Prior Publication Data

US 2014/0186789 A1 Jul. 3, 2014

Related U.S. Application Data

(60) Provisional application No. 61/746,326, filed on Dec. 27, 2012.

(51) Int. Cl.
*A61C 7/00* (2006.01)
*A61C 7/08* (2006.01)

(52) U.S. Cl.
CPC ............... *A61C 7/008* (2013.01); *A61C 7/08* (2013.01)

(58) Field of Classification Search
CPC .. A61C 7/08; A61C 7/008; A61C 7/10; A61C 9/00–9/0006
USPC ................ 433/2, 18, 24, 215, 118, 119; 128/859–862; 482/11
See application file for complete search history.

(56) References Cited

U.S. PATENT DOCUMENTS

| | | | |
|---|---|---|---|
| 4,348,178 A * | 9/1982 | Kurz | 433/6 |
| 5,203,695 A * | 4/1993 | Bergersen | 433/6 |
| 2008/0227046 A1 | 9/2008 | Lowe | |
| 2008/0227047 A1 | 9/2008 | Lowe | |
| 2009/0165805 A1* | 7/2009 | Syrop et al. | 128/861 |
| 2010/0055634 A1* | 3/2010 | Spaulding et al. | 433/5 |
| 2012/0322018 A1 | 12/2012 | Lowe | |

* cited by examiner

*Primary Examiner* — Edward Moran
(74) *Attorney, Agent, or Firm* — Boulware & Valoir

(57) ABSTRACT

Improved shapeable bite plates for use with orthodontic vibratory devices and devices offering other treatment modalities. The shapeable bite plates can be manually shaped to fit the Euro arch, arch form I, the Roth arch, and even widest Damon Arch.

15 Claims, 6 Drawing Sheets

SHAPEABLE BITE PLATES

PRIOR RELATED APPLICATIONS

This application claims priority to U.S. Ser. No. 61/746,326, filed Dec. 27, 2012, and expressly incorporated by reference herein.

FEDERALLY SPONSORED RESEARCH STATEMENT

Not applicable.

FIELD OF THE INVENTION

This invention relates to shapeable bite plates that can be used with any device used for orthodontic remodeling.

BACKGROUND OF THE INVENTION

A malocclusion is a misalignment of teeth or incorrect relation between the teeth of the two dental arches. The term was coined by Edward Angle—the father of modern orthodontics—as a derivative of occlusion, which refers to the way opposing teeth meet. Angle based his classifications of malocclusions on the relative position of the maxillary first molar. According to Angle, the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variations therefrom is a malocclusion.

There are three classes of malocclusions, Class I, II, and III. Further, class II is subdivided into three subtypes:

Class I: Neutrocclusion The molar relationship of the occlusion is normal or as described for the maxillary first molar, but the other teeth have other problems like spacing, crowding, over or under eruption, etc.

Class II: Distocclusion (retrognathism, overjet) In this situation, the upper molars are placed not in the mesiobuccal groove, but anteriorly to it. Usually the mesiobuccal cusp rests in between the first mandibular molars and second premolars. There are two subtypes:

Class II Division 1: The molar relationships are like that of Class II and the anterior teeth are protruded.

Class II Division 2: The molar relationships are class II, but the central incisors are retroclined and the lateral incisors are seen overlapping the central incisors.

Class III: Mesiocclusion (prognathism, negative overjet) In class III mesiocclusions the upper molars are placed not in the mesiobuccal groove, but posteriorly to it. The mesiobuccal cusp of the maxillary first molar lies posteriorly to the mesiobuccal groove of the mandibular first molar. This malocclusion is usually seen when the lower front teeth are more prominent than the upper front teeth. In such cases, the patient very often has either a large mandible or a short maxillary bone.

Orthodontics, formerly orthodontia (from Greek orthos "straight or proper or perfect" and odous "tooth"), is the first specialty of dentistry that is concerned with the study and treatment of malocclusion, which can be a result of tooth irregularity, disproportionate facial skeleton relationship, or both. Orthodontics treats malocclusion through the displacement of teeth via bony remodeling and control and modification of facial growth.

This process has been accomplished for thousands of years using static mechanical force to induce bone remodeling, thereby enabling teeth to move. In fact, archaeologists have unearthed ancient mummies that have crudely constructed bands of metal around their teeth.

In modern orthodontics, braces consisting of an archwire interfaces with brackets that are affixed to each tooth. As the teeth respond to the pressure applied via the archwire by shifting their positions, the wires are again tightened to apply additional pressure. This widely accepted approach to treating malocclusion takes about twenty-four months on average to complete, and is used to treat a number of different classifications of clinical malocclusion.

Treatment with braces is complicated by the fact that it is uncomfortable and/or painful for patients, and the orthodontic appliances are perceived as unaesthetic, all of which creates considerable resistance to use. Additionally, the 2 year treatment time is very long and cannot be shortened by increasing the force, since too high a force is both painful and leads to tooth resorption. In fact, some estimates provide that less than half of the patients who could benefit from such treatment elect to pursue orthodontics.

Kesling introduced the tooth positioning appliance in 1945 as a method of refining the final stage of orthodontic finishing after removal of the braces (debanding). The positioner was a one-piece pliable rubber appliance fabricated on the idealized wax set-ups for patients whose basic treatment was complete.

Kesling also predicted that certain major tooth movements could also be accomplished with a series of positioners fabricated from sequential tooth movements on the set-up as the treatment progressed. However, this idea did not become practical until the advent of 3D scanning and computer modeling in 1997, when the Invisalign® system was introduced by Align Technologies®.

In addition to static forces, cyclic forces can also be used for orthodontic remodeling. Kopher and Mao assessed cyclic forces of 5N peak magnitude at 1 Hz in rabbits, while Peptan and Mao assessed cyclic forces of 1N at 8 Hz in rabbits, and Vij and Mao assessed cyclic forces of 300 mN at 4 Hz in rats. In aggregate, the data from these three studies indicated that cyclic forces between 1 Hz and 8 Hz, with forces ranging from 0.3N to 5N, increased bone remodeling. Rates depended on different methodologies, but increases of up to 2.5× with vibrational forces were common.

Since Dr. Mao's experiments, an independent study out of Japan has confirmed and strengthened the idea of vibration at 60 Hz for speeding orthodontic tooth movement, and an earlier 50 Hz study in Russia also confirms the basic premise. In fact, by now there is a well established literature confirming the efficacy of this treatment modality.

The early Mao studies provided a basis for both possible efficacy and likely safety for using vibration in humans to assist orthodontic tooth movement, but the animal studies needed to be repeatable in humans, and the devices used by Mao and the others were completely unsuitable for clinical work.

OrthoAccel® Technologies Inc., invented the first commercially successful dental vibrating device, as described in US2008227046 and related cases, designed to apply cyclic forces to the dentition for accelerated remodeling purposes. Both intra-oral and extraoral embodiments are described in US2008227046, each having processors to capture and transmit patient usage information.

The bite plate was specially designed to contact occlusal as well as lingual and/or facial surfaces of the dentition, and thus was more effective than any prior art devices in conveying vibrational forces to the teeth. Further, the device was tested in clinical trials and has been shown to speed orthodontic remodeling as much as 50%, and is truly a breakthrough in orthodontic technology (Kau 2010).

Finally, the device is slim, capable of hands free operation, lacks the bulky head gear of the prior art devices, and has optimized force and frequency for orthodontic remodeling. Thus, its comfort level and compliance was also found to be high, with patients reporting that they liked the device, especially after the motor was redesigned to be quieter and smoother, as described in US2010055634 et seq. In fact, this device has been marketed as AcceleDent® in the United States, and several other countries and has achieved remarkable commercial success since its recent introduction. AcceleDent® represents the first successful clinical approach to accelerate orthodontic tooth movement by modulating bone biology in a non-invasive and non-pharmacological manner.

Although compliance with the AcceleDent® is fairly good, with certain patients compliance is less than satisfactory. In investigating the basis for non-use, OrthoAccel® discovered that a poorly fitting bite plate reduced compliance because the extraoral vibratory source, coupled with a poorly fitting bite plate, resulted in excessive salivation, which tended to egress from the oral cavity. Patients with poorly fitting bite plates were more likely to have poor compliance records. In addition, the original bite plate was shaped to fit the classic "Euro arch" which is narrower in form than many Asian arches. Thus, the original devices tend to fit the Asian patient, or patients with the Damon arch (an even wider arch form) less well.

WO2011056260 attempted to solve this problem with a series of bite plates in a small, medium and large size together with open, flat and deep bite plate architecture, thus providing a series of 9 bite plates that fit a significant percentage of the population. While this solution is one viable option, it requires tooling up and inventory for a substantial number of bite plates, and further still is less than a perfect solution for the wider arches, since it was still based on the Euro arch.

Another option is to make the bite plate with a shapeable material, such as the boil and bite mouth guards. U.S. application Ser. No. 13/967,043, filed Aug. 14, 2013 describes a bite plate having a bead of light curable resin thereon, which can be shaped once by the patient, and then uv light cured in the orthodontic office. This option, however, requires that inventory be protected from light, and long term stability might be an issue. Further, once shaped it cannot be reshaped, therefore as treatment progresses new bite plates will be needed.

Custom dental appliances are, of course, readily available, as indicated by the aligner and positioner markets. However, these products require 3D modeling and/or custom impressions made of the dentition and some time in an offsite laboratory facility to make the custom fitted appliance. Alternatively, the practitioner can make his own devices, e.g., with a 3D printer, but again lab time is needed, thus contributing to inefficiencies.

Therefore, what is needed in the art is a shapeable bite plate that can be individually fitted to each patient, without a significant time investment needed by the patient or practitioner, and without a significant inventory commitment by distributors. This application addresses some of those needed improvements.

SUMMARY OF THE INVENTION

The invention is directed to a shapeable bite plate that has a shapeable core, such that the patient can shape the bite plate to fit his or her individual dentition.

At a minimum, the bite plate is shaped to fit the classic Euro arch, and for those patients with a wider arch, the bite plate can be pressured by the patient, or the orthodontist, into a wider arch form as needed. The reverse is also possible.

The shapeable bite plate has an inner core that is made of e.g., metal, such as a heavy gauge wire (e.g. 8-16 gauge), or of a soft temper material, such as a half-hard material. Alternatively, multiple strands of finer wire>16 gauge can be braided or twisted together and used. A planar metal strip could also be used in place of wire, and in some embodiments is arranged vertically, positioned inside e.g., the outer flange of the bite plate. In some embodiments, the metal strip is shaped with one or two or more wedges, such that the wedges can be widened, thus changing the curvature of the core, and the metal strip can thus be positioned in a flat horizontal orientation between the occlusal surfaces of teeth. In yet other embodiments, a wire travels back and forth, creating a strip like flat core in outline that can easily be reshaped. In yet other embodiments, combinations of the above are used.

The metals may be selected from aluminum, nickel, copper, stainless steel, cobalt, vanadium, chromium, iron, and alloys of same, provided that the gauge and material combination still be shapeable under human hand forces, and hold that shape under conditions of use. Obviously, if a heavier gauge wire is used, a softer temper would be required than if a thinner wire is used.

| METRIC-TO-AWG CONVERSION TABLE | |
|---|---|
| Metric Size mm$^2$ | AWG Size |
| 0.5 | 20 |
| 0.8 | 18 |
| 1.0 | 16 |
| 2.0 | 14 |
| 3.0 | 12 |
| 5.0 | 10 |
| 8.0 | 8 |

In prior art bite plates for vibration treatment modalities, the core was flat and sufficiently stiff so as to transmit vibration to the mouthpiece and thence to the teeth. However, even with a shapeable wire, sufficient vibration can be transmitted to the teeth for efficacy, and it is also possible to increase the force levels to account for the small (e.g., 10-25%) amount of dampening that may occur.

The shapeable core is connected to or integral with a connector, which serves to connect the bite plate to an extraoral driver. The connector can be of any suitable shape, but preferably provides a snap fit to the extraoral driver. The connector can be integral with the shapeable core, but more likely will be a separate component attached thereto. Means of connecting wires or metal strips to other components is well within the skill in the art, and include e.g., welding, screws, rivets, snap fits, adhesives, etc.

The shapeable core is covered with a hermetically sealed polymeric coating or cover, wherein the outer surface thereof is shaped to contact occlusal and facial and/or lingual teeth surfaces, and has enough flexibility to allow the shapeable core to be moved as much as one cm. A harder material can be used, if, for example, the material is made temporarily softer, e.g., with heat or steam, so as to allow the reshaping process, but this is not currently preferred as contributing to complexity of use.

If desired, additional coatings can be applied thereto, e.g., a soft, tasteless coating can be provided over an otherwise suitable material that has unpleasant taste. Silicone is known to provide a material with the desired characteristics, but additional polymers are known, and some are described below.

The bite plate is combined with any other treatment modality, including vibration, laser light, IR light, electromagnetic pulses, electrical micropulses, heat, and the like. The shapeable bite plate is preferably used with the existing extraoral vibrational device, which is already cleared for marketing in the US and several other places and already has proven efficacy. In addition, the same principles can be applied to a completely intra-oral device, wherein the vibratory source or other treatment modality, power source and wiring are mounted directly on the bite plate.

The bite plate can be assembled using the shapeable core, which is generally U-shaped in outline to contact the occlusal surfaces of the Euro arch (e.g., narrowing as it progresses from the posterior (molar) to the anterior (incisor) teeth. If intraoral, the components are placed on the core, which is coupled to the connector, then the entire assembly is covered with the polymeric covering, thus hermetically sealing or waterproofing the components against water ingress.

The bite plate preferably also has a vertical edge (aka rim or phalange) to contact at least one of the facial and lingual surfaces, especially for a vibrational treatment modality, as this allows the vibration to be in an up-and-down direction, as well as front-to-back direction. The vertical edges thus allow the vibration to be transferred to the teeth in two axes, and are much preferred over a simple flat bite plate. The edges also serve to keep the bite plate correctly positioned over the teeth during use.

The preferred polymer for the bite plate has no taste or toxicity, does not leach components, and is preferably tested for same before use according to known tests. Where a polymer does leach, it can be coated with a sealant, but a non-leaching polymer is preferred since sealants have a limited lifespan in an oral environment.

The most preferred materials are medical grade or FDA cleared for oral use and are tasteless, non-toxic, and biocompatible. Suitable resins may include an epoxy, a cyanoacrylate, an acrylate, a urethane, an acrylate and urethane mixture, a urethane oligomer/(meth) acrylate monomer blend resin, a silicone, a silicone copolymer, or a copolymer of hydrogen siloxanes and unsaturated compounds. Silicone is particularly preferred.

Alternatively, the resin may comprise copolymers of hydrogen siloxanes and unsaturated compounds. These may be used as adhesion promoters to build a chemical link between the resin and the shapeable core. An example of such an adhesive is described in DE19934117 and incorporated by reference herein for all purposes. Other resins are described in e.g., U.S. Pat. No. 5,856,373; 2011/0200973; U.S. Pat. Nos. 5,017,626; 4,459,193; 4,411,625; 4,771,084; US20050049326.

The current polymers are clear, but colored pellets can be added to the polymer in the molten form, this making colored bite plates, which can appeal to younger patients. If desired, the outer surfaces can also be imprinted with designs, and if needed for longevity can be coated with a sealant.

By "U-shaped" what is meant herein is that the bite plates follow the curvature of the dentition, e.g., the biting surfaces of the teeth are in a substantially U-shaped curvature.

By "U-shaped in outline," what is meant is that if a line traces the outmost reach of the core, it is generally U-shaped to follow the human dental arch, even if portions inside the U-shape are omitted as with wedge cutouts or bent wires.

By "lingually shaped" what is meant is shaped like a tongue, or filled in U-shape.

By "molar end" what is meant is the end (typically two) of the bite plate that contact the molars or premolars.

By "Euro arch" or "Euro form" herein what is meant is a dentition that narrows from the molars to the incisors. In contrast, other arch forms may be much rounder, or even having parallel sides, and not begin to narrow until closer to the front of the dentition.

By "shapeable" what is meant herein is that the form can be shaped with the force applied by an average adult human hand, and that the shape is thereafter retained during normal use, such that the bite plate needs be adjusted to fit once at the beginning of treatment, and perhaps minor adjustments made as the orthodontic treatment progressively moves the teeth into alignment and/or occlusion.

By "bend of at least one cm towards or away from a midline of said U-shape" we refer to the molar ends of said bite plate moving one cm away from a midline. Thus, e.g., if each end moves one cm from the midline, the ends are a total of 2 cm farther apart. This degree of motion will accommodate most of the human population.

When we refer to contacting "the teeth" or similar phrase herein, what is meant the teeth of both arches, unless the maxillary teeth or mandibular teeth are specifically referred to separately. Nevertheless, the bite plate need not contact every single tooth, since by definition some malocclusions may results in one or more teeth considerably out of position.

By "treatment modality" what is meant is a mode of action that causes a orthodontic, hygienic, aesthetic or medical benefit.

By "treatment modality source," what is meant is a device or component of a device that provides the treatment modality. For example, vibration is an orthodontic treatment modality and a vibratory source provides vibration. A vibratory source could also be called a vibrator. Another treatment modality is infrared or ultraviolet light, and an LED could be an exemplary light source.

An "extraoral driver" is the extraoral component that provides the treatment modality, and in preferred embodiments is a housing having an e.g., a treatment modality source such as a vibrator or laser, a processor, a battery or other power source, and the wiring needed to operatively couple or operate same, and wherein the housing has a socket for receiving the connector of the bite plate. The housing should of course be water resistant or waterproof.

By "flexible" herein in reference to the polymeric coating or covering, what is meant is that the polymer has enough flex in it to allow the shapeable core ends to be bent at least plus or minus one cm from the midline.

By "daily" what is meant is at least 67% compliance in daily use. Although perfect compliance would obviously be preferred, significantly increased speed of orthodontic remodeling was seen at only 67% compliance in the Kau study.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term "consisting essentially of" excludes only material elements, such as bulky headgear.

BRIEF DESCRIPTION OF THE DRAWINGS

FIG. 8A is the top view, FIG. 8B is the front view and FIG. 8C is the side view.

DETAILED DESCRIPTION OF THE INVENTION

Figure 1A:
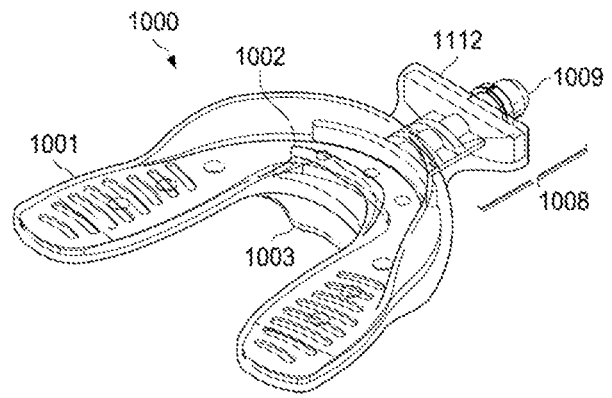
FIGS. 1A and 1B show a perspective view of a prior art bite plate from two different angles.

The disclosure describes a shapeable bite plate, preferably having the characteristics of the special prior art bite plates described in US2008227046, US2008227047, US2010055634, Ser. Nos. 13/609,346, 61/624,242, 61/615, 480 and 61/673,236 and intended to be used with intra-oral or extraoral vibratory or other treatment modality sources, as described in the preceding applications for patent, each incorporated by reference in their entireties.

In some embodiments, a bite plate for an orthodontic remodeling device is provided, said bite plate comprising:
  (a) a shapeable metal core that is U-shaped in outline to follow the curvature of a dental arch;
  (b) said metal core covered with a flexible biocompatible polymer;
  (c) said flexible biocompatible polymer shaped to have an outside edge having upper and lower rims to contact upper and lower facial surfaces of teeth;
  (d) said flexible biocompatible polymer having an inside edge having optional upper and lower rims to contact at least a portion of upper and lower lingual surfaces of teeth;
  (e) said metal core and covering being able to bend such that a molar end of said bite plate can move at least one cm towards or away from a midline of said bite plate;
  (f) wherein the bite plate has a connector thereon for reversibly coupling to an extra-oral orthodontic remodeling device.

The metal core provides at least a U-shaped framework that follows the curvature of the human arch. It can also provide one or more rims in some embodiments. In other embodiments, the rims are made only of polymer, not having a metal core.

The metal core can be 8-16 gauge wire, or smaller, or a 10-12 gauge wire. Alternatively, it can be a planar metal U-shaped strip having a plurality of wedge shaped openings along one or more edges thereof. In yet another alternative, the core is a wire that is bent in a single plane in e.g., a back-and-forth pattern to form said U-shape.

In another embodiment, the disclosure provides a wholly intra-oral orthodontic remodeling device comprising a vibrating bite plate, said bite plate comprising:
  (a) a metal core that is substantially U-shaped in outline to follow the curvature of a dental arch, said core having a plurality of spreadable wedges or wedge cutouts on an edge thereof, such that the curvature can be changed by a patient;
  (b) a flexible biocompatible covering on said metal core;
  (c) said flexible biocompatible covering having an outside edge having upper and lower rims to contact upper and lower facial surfaces of teeth;
  (d) said flexible biocompatible covering having an inside edge having optional upper and lower rims to contact at least a portion of upper and lower lingual surfaces of teeth;
  (e) wherein said metal core has a vibrator on a surface thereon operably coupled to a battery or charge capacitor and wherein said vibrator and battery or charged capacitor are hermetically sealed;
  (f) said metal core and flexible biocompatible covering are flexible enough to allow a bend such that a molar end of said bite plate can move at least one cm towards or away from a midline of said bite plate.

Other embodiments provide a shapeable bite plate comprising a shapeable metal core and a flexible biocompatible covering, wherein said shapeable metal core is a planar piece of metal with a plurality of wedge cutouts in an edge thereof or a wire or a wire that travels back and forth in a planar path. As above, the shapeable metal core and flexible biocompatible covering allow a bend such that a molar end of said bite plate can move at least one cm towards or away from a midline of said bite plate.

In some embodiments, the shapeable core is a 8-16 gauge metal wire, and in others it is a metal strip. If desired, the core can also have vertical rims.

In other embodiments, the rims can be omitted entirely, but having at least one rim to contact facial or lingual teeth surface is preferred for comfort, placement (having at least one rim helps to hold the device in place), and adequate force transmission in a vibratory device.

In yet other embodiments, the bite plate has fitted therein one or more e.g., coin vibrators or other tiny vibratory source(s), which is operably coupled to one or more coin battery(s) or charged capacitor(s), which are operably coupled to an optional processor for controlling the device and monitoring usage compliance. Thus, the entire device is intra-oral and of customizable fit.

In yet other embodiments, the device uses other treatment modalities in place of or in addition to pulsed or cyclic forces (aka vibration). Thus, the device can be fitted with IR light source, EM field source, microelectronic pulse source, and the like. However, in preferred modalities, the device includes a vibrational source, since vibration has already been proven in clinical trials to reduce remodeling time by 50%.

Figure 1B:
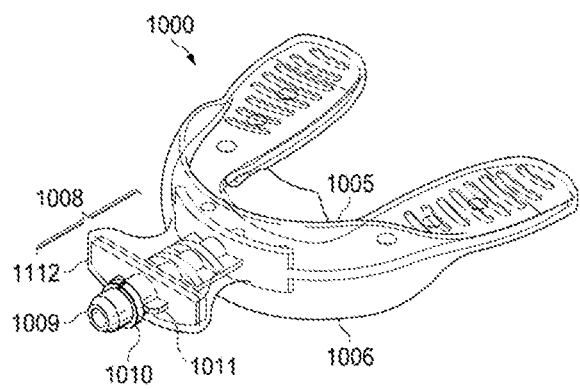
Figure 1C:
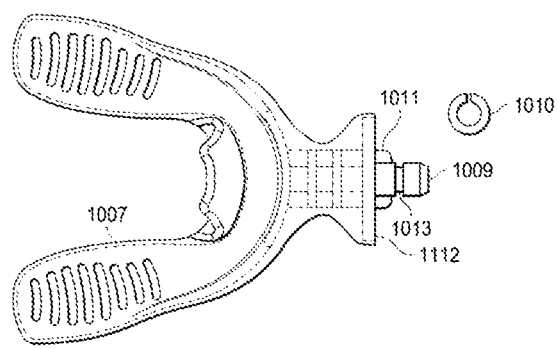
FIG. 1C shows the same prior art bite plate from a top plan view.

FIG. 1A-C shows a prior art bite plate (1000) from two angles 1A-B, as well as a top plan view 1C. Here the bite plate has a generally U-shaped base (1001) that contacts occlusal surfaces of the teeth, the bite plate having front (outer edge of the U) and back (inner edge of the U) edges, one or both edges having a rim to contact the facial and lingual surfaces of teeth and/or gums. Thus, upper lingual rim (1002), lower lingual rim (1003), upper facial rim (1005) and lower facial rim (1006) are shown. In this instance, the lingual rims contact only the incisors, canines, and premolars, but not the molars. It is preferred that at least one rim contact each tooth (except for recessed teeth). However, some flexibility in the degree of molar contact is acceptable, since children lack one or all molars and the full complement of molars may not erupt until the mid twenties or molars can be removed due to overcrowding.

Also shown is the stem (1008), which is the portion of the bite plate (1000) that mates with a corresponding socket in the extraoral housing (not shown here), which contains the power source, vibratory source or other treatment modality source, processor for controlling the device and optionally for providing optional compliance features, optional off-on switch, optional indicator lights for power and/or usage and/or time of usage, and the like.

In more detail, a cylindrical shaft (1009) is shown, having a groove (see FIG. 1C) into which a spring or jump ring (1010) fits, and mates with a corresponding depression in the socket. Optional flare (1112) is also shown, and is configured to provide an appropriate surface (dumbbell curve) so that the user can push the stem into the socket.

FIG. 1C shows a top plan view of the bite plate, more clearly illustrating the core (1007), shaft (1009), flare (1112), pins (1011) and jump ring (1010), as well as the other edge of the overcoat, which provides the actual shape of the bite plate.

Figure 2A:
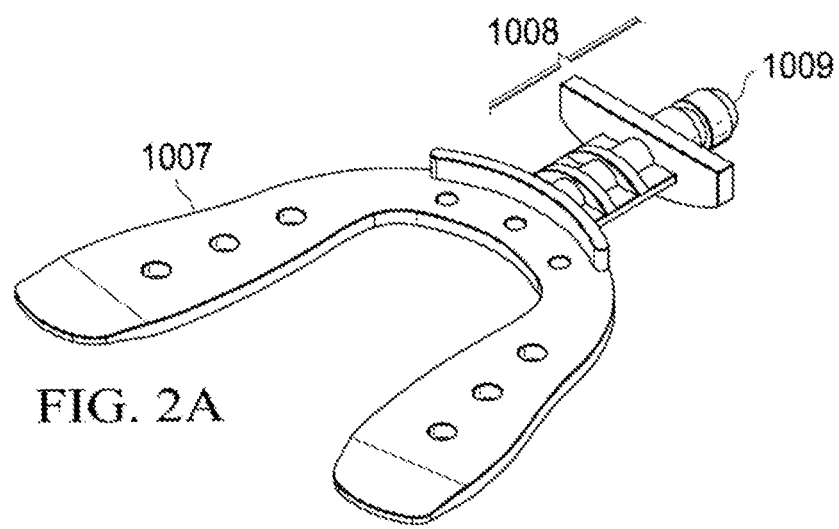
FIG. 2A-B shows a perspective view of the inner core of the prior art bite plate from two different angles. This bite plate does not allow any significant amount of flex.
Figure 2B:
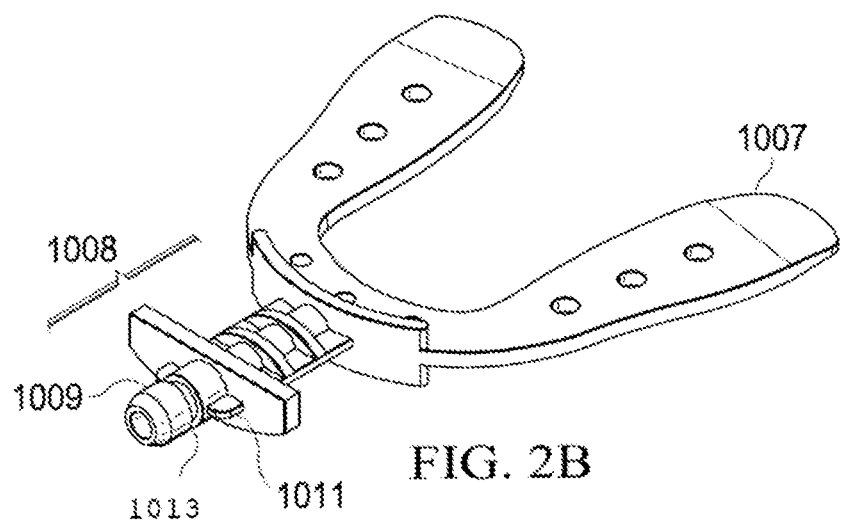

FIG. 2 shows just the core (1007) of the prior art bite plate, typically made from a resin, metal or ceramic having a harder durometer than the outer surface, and providing sufficient rigidity to the stem (1008) so as to allow it to lockingly fit into the socket. Cylindrical shaft (1009) has a groove (1013), into which jump ring (1010) fits. Also seen are locking pins (1011) that can also function as orientation pins if asymmetric, to prevent the bite plate from being inserted upside down. Generally plastics of at least 40 Shore D were used for the prior art core, but metals or ceramics could also be used. A coating is provided over this core, and provides the final shape of the bite plate, as shown in FIG. 1. Such coating should be a biocompatible soft polymer of 40-70 Shore A, and particularly preferred is a medical grade, clear silicone.

Figure 3:
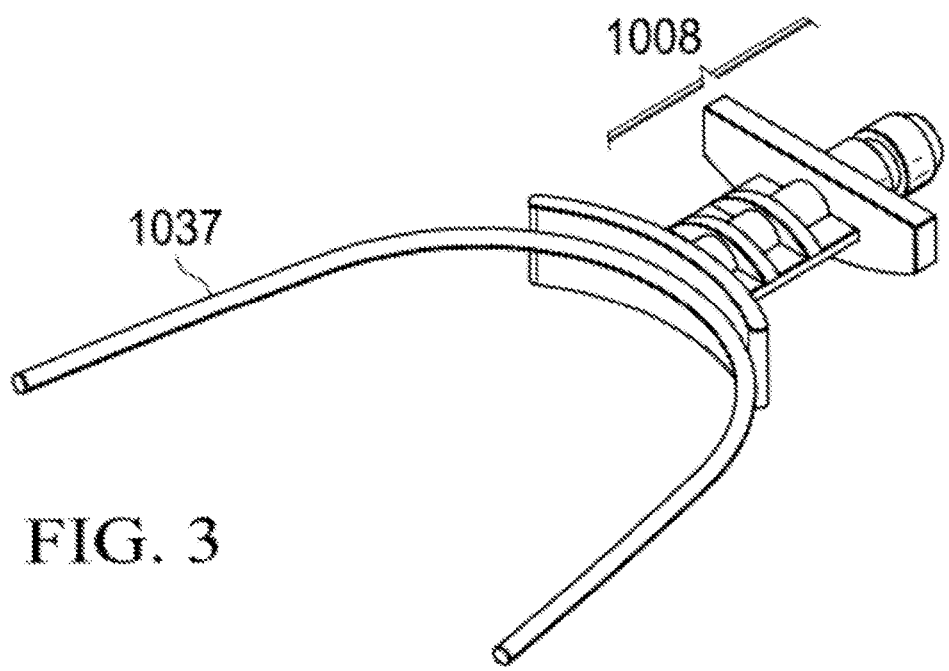
FIG. 3 shows a wire core that can be shaped to fit the patient.

FIG. 3 shows a bite plate core wherein the shapeable core (1037) is a bendable wire connected to the same connector (1008). The gauge of wire will vary with the softness or temper of the metal or alloy chosen, but typically might be in the 8-16 gauge range, or 10-12 gauge range.

Figure 4:
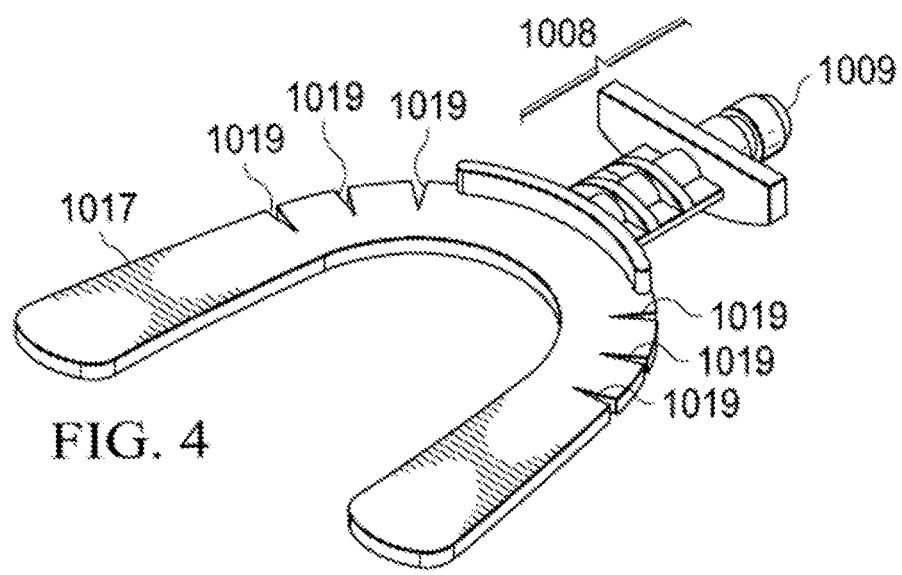
FIG. 4 shows a flat strip core with wedge cutouts on the e.g., outer edge. In use, the patient can close up the wedges, making the bite plate wider, or widen the wedges, making it narrower. Shown here are six wedges, but the number and placement can be varied.

FIG. 4 shows a flat metal core (1017), wherein wedges (1019) are cut out of the core (or otherwise provided), allowing the reshaping of the curvature of the bite plate to fit the patent.

Figure 5:
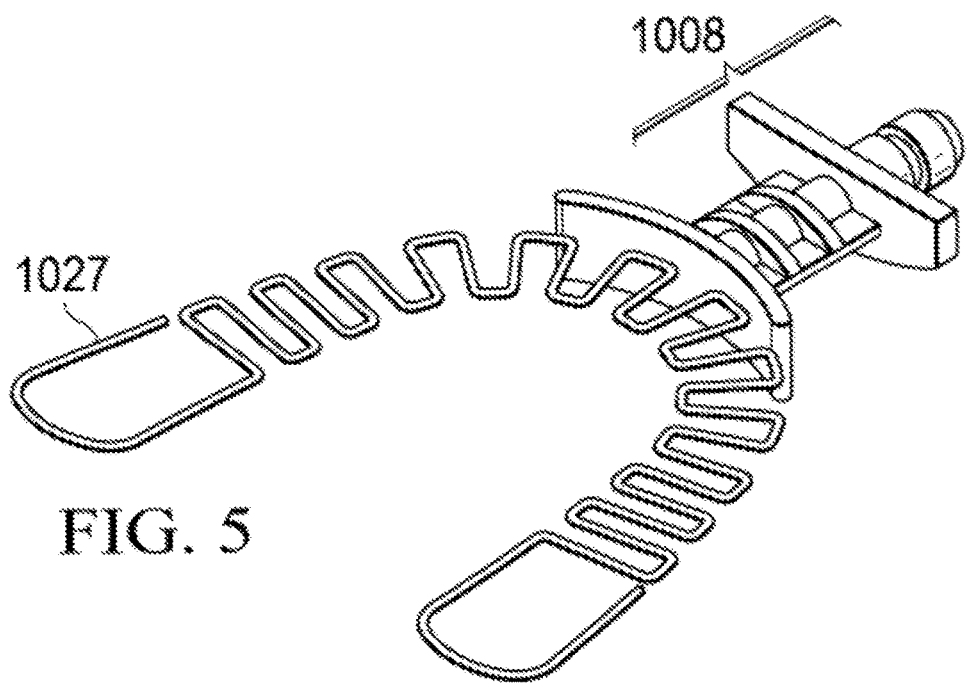
FIG. 5 shows a bent wire shaped to form a flat core, wherein the wire bending can be in a sine wave pattern, peak and trough pattern, or square wave, or variations therebetween. Here shown is a square wave like pattern.

FIG. 5 shows an embodiment similar to FIG. 4 where the wedge cutout idea is taken to its logical limit. Here, a bent wire (1027) where the wire travels back and forth to make a large number of spreadable cutouts. Shown is a wire bent in a square wave pattern to make the overall form of the flat bite plate. Each of the squares can be opened a bit on the inner edge, thus widening the bite plate. Thus, as can be seen, the term "wedge" herein can include a square wedge, a pie shaped wedge, or variations thereof, the point being that a shapeable wedge can be spread wider or squeezed more narrowly to change the curvature of the bite plate. For a higher degree of curvature, more wedges are added. Further, although FIG. 5 shows the core made with a single wire, obviously, additional wires can be applied in similar patterns, the wires interleaving (passing over and under each other), so as to provide additional strength, yet retaining the flexibility needed for reshaping.

Figure 6:
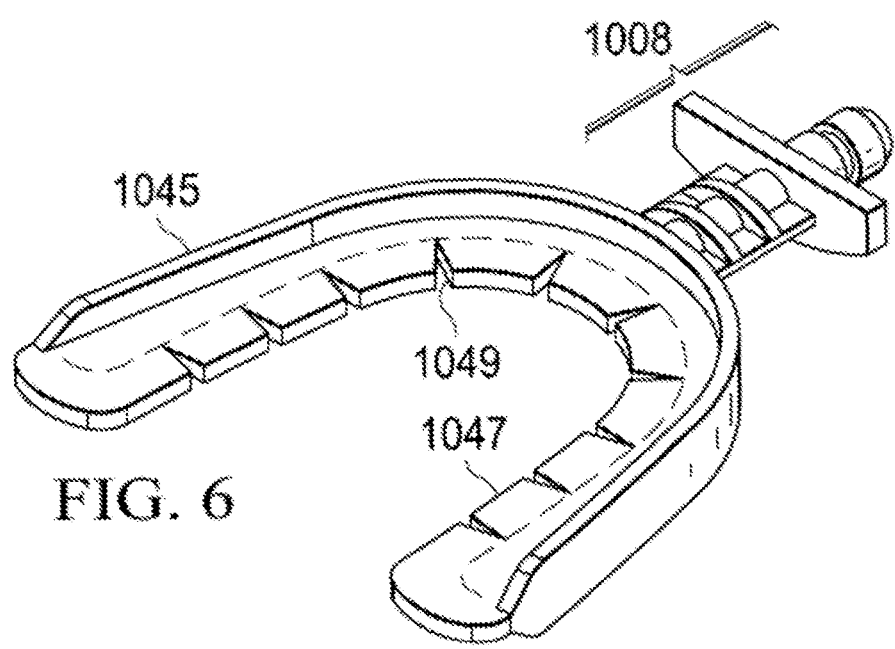
FIG. 6 shows a flat core where the wedges are on the inner edge thereof, and the flat core has facial rims protruding above and below the flat portion.
Figure 7A:
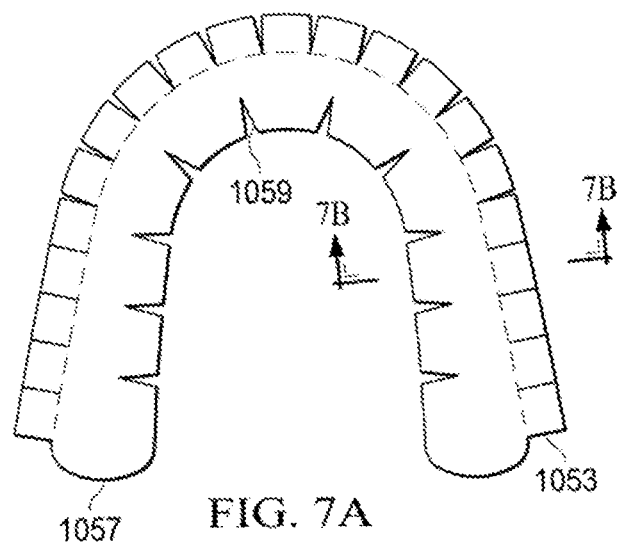
FIG. 7A-D shows a pattern for a flat core that can be stamped from a sheet of metal, such as aluminum. The leaves are bent upwards (see FIG. 7B) during manufacture to create a vertical rim. Two of such sheets can be used to provide a facial rim that contact both upper and lower teeth, and the sheet can be glued, rivet or welded together, or even just positioned adjacently (7C). Alternatively, additional leaves can be e.g., welded to otherwise attached to the other side of the flat portion (7D).
Figure 7B:
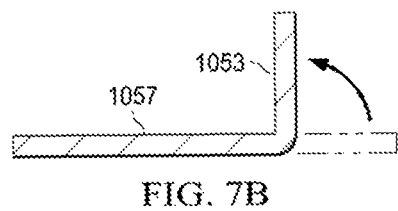
Figure 7C:
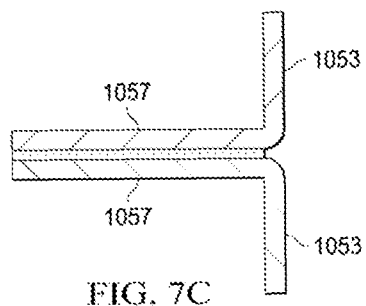
Figure 7D:
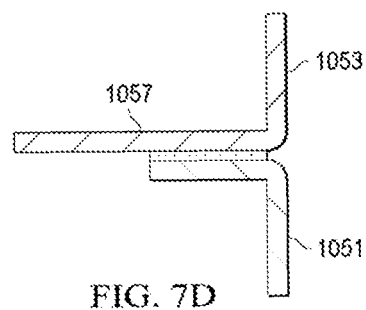

FIG. 6 shows a flat core (1047) with an outer rim (1045) to contact the facial surfaces of both upper and lower teeth. Cutouts (1049) allow this shape to be bent to fit the curvature of the teeth.

FIG. 7 shows a flat pattern for a core, wherein the facial rim leaves or tabs (1053) can be bent up to contact facial surfaces. Obviously, one or more leaves can be omitted to change the length of the vertical rims. If two of such templates are used, the flat occlusal surfaces being adjacent, then the entire core can be punched from a flat sheet of metal, reducing manufacturing costs. Since the leaves can be individually adjusted, such an embodiment may be of particular use where a patient has one tooth overlapping another, e.g., a severely protruding incisor or canine In this embodiment, the wedges (1059) are on the inner edge (lingual) of the bite plate. If preferred, a single sheet can be used, wherein additional leaves or flaps (1051) can be welded or glued to the bottom surface thereof for contacting the other arch.

Although not shown herein, each of the embodiments of FIG. 3-7 have a polymeric coating or covering that can be shaped, e.g., as in FIG. 1. Furthermore, the connector preferably fits with existing devices, such as the AcceleDent®.

As can be seen, in each of the embodiments the core is generally U-shaped in outline, following the arch of the dentition. Preferably, the device is manufactured and sold in a Euro arch form, thus fitting the majority of North American and European patients, and is then widened as needed for patients with the wider arch forms. However, it is also possible to reverse the two, making the device in a wider form and narrowing it to fit certain patients, and such may be desirable, e.g., in an Asian market.

This shapeable design solves the problem of having a bite plate to fit a wide range of arch shapes; however, the practitioner or distributor will still need to keep some inventory, since different sizes must be provided for children and adults. Thus, the practitioner will stock the shapeable bite plate in small and large, and possible also in a medium size. However, this is a big improvement over having each size available in the 4 common arch forms, leading to 12 separate bite plates. In practice, the curvature of the shapeable bite plate herein described is infinitely variable.

It is preferred that the bite plate have a connector that is completely compatible with existing drivers, being of the same size and proportions. Using similar connectors allows the bite plates to be interchangeable, and also allows any bite plate inventory to be used even when the driver unit model is updated. Thus, these sizes are valuable for interchangeability of parts. The minimum for interchangeable parts based on the current models requires the cylindrical post to be about 10.25 mm in length and about 6.35 mm in diameter mm with a groove about 4 mm from the attached end of the post.

Figure 8A:
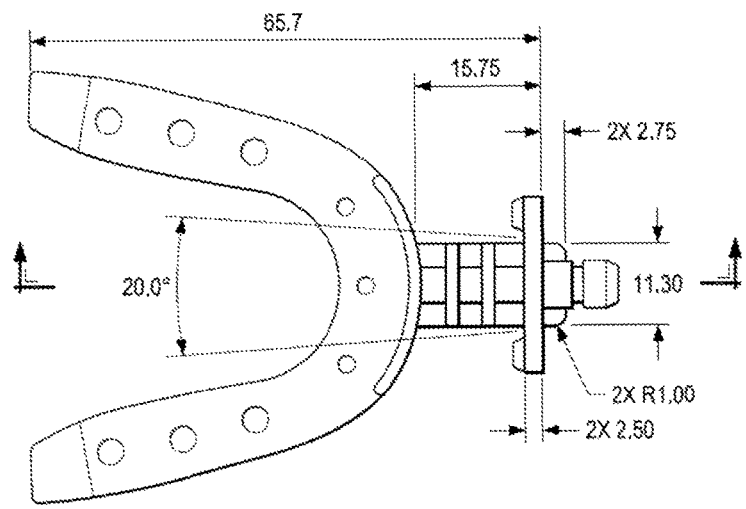
FIG. 8A-C shows the dimensions of the commercial connector, which if followed, allows the inventive bite plate to be used with the existing vibratory driver.
Figure 8B:
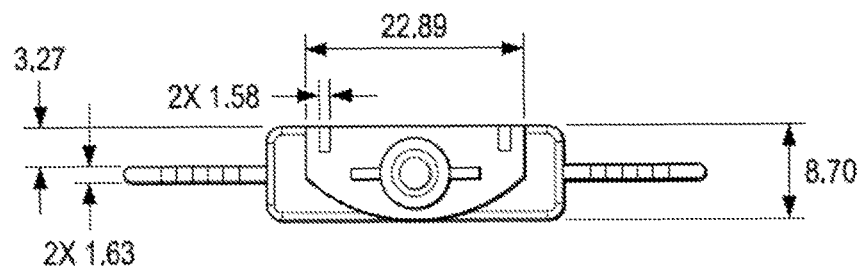
Figure 8C:
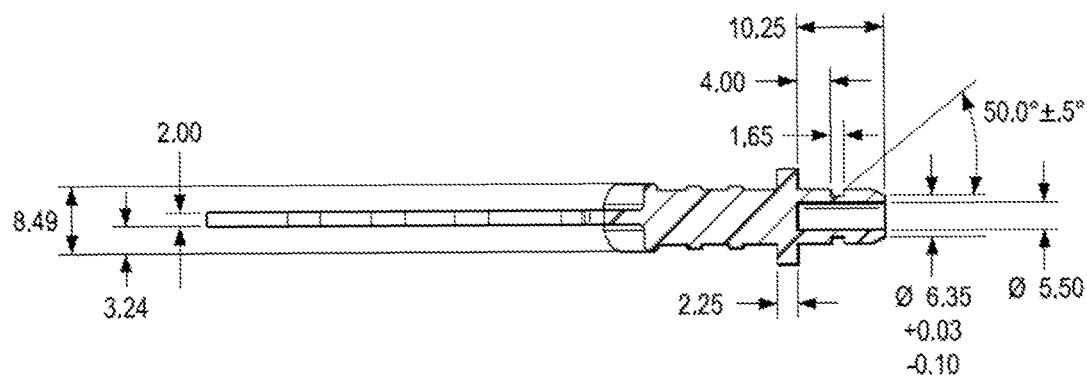

The connector in FIG. 8A-C has a flat surface opposite the bite plate, from which protrudes a centrally positioned cylindrical post that is 6-7 (6.35+0.03, −0.1 tolerances indicated) mm in diameter, 10-11 (10.25) mm in length, and having a groove circumventing the post about half way (4 mm from flat surface, with width of 1.65 mm).

The bottom of the post also has a pair of ~1.4×3 mm pins (optional) projecting 180° from each other (in the same plane as the occlusal contacting base of the bite plate). These pins have a total spread of 11.30 mm at the topmost edge, but flare 10° on each side (20° total) to reach the flat surface of the base. The pins are 1.63 mm thick, and 2.75 mm high.

The base of the connector also preferably has a pair of recessions ~1.5 mm wide×3 mm long×2 mm deep (1.58× 3.27×2.5 mm) on the flat surface thereof for engaging clips from the driver, the recessions being about 16-17 mm apart (22.89 mm in spread), and positioned right below the pins. The recessions can be omitted however, if the base is either not flared or is otherwise smaller, such that the remaining post and pins still fit, leaving the engaging clips on the driver free. These dimensions are approximate, and exact dimensions are provided on FIG. 8A-C.

The following are incorporated by reference here in their entireties.

US2008227046, US2008227047, US2010055634, Ser. Nos. 13/609,346, 61/624,242, 61/615,480 and 61/673,236.

Kau, et al., The clinical evaluation of a novel cyclical force generating device in orthodontics, Orthodontic Practice 1(1) (2010).

While the invention is described above in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. An orthodontic remodeling device, comprising a bite plate and an extraoral driver, said bite plate comprising:
   i) a shapeable metal core having a flat U-shape in outline to fit between occlusal surfaces of teeth;
   ii) said metal core covered with a flexible biocompatible polymer;
   iii) said flexible biocompatible polymer shaped to have an outside edge having upper and lower rims to contact an upper and lower facial surfaces of teeth;
   iv) said flexible biocompatible polymer having an inside edge having optional upper and lower rims to contact at least a portion of an upper and lower lingual surfaces of teeth;
   v) said metal core and flexible biocompatible polymer being sufficiently flexible to bend such that a molar end of said bite plate can move at least one cm towards or away from a midline of said bite plate;
   vi) wherein the bite plate has a connector thereon for reversibly coupling to said extra-oral driver; and,
   vii) wherein said extraoral driver vibrates said orthodontic remodeling device to accelerate orthodontic remodeling.

2. The orthodontic remodeling device of claim 1, wherein said core is a wire.

3. The orthodontic remodeling device of claim 1, wherein said core is a planar metal U-shaped strip having a plurality of wedge shaped openings along one or more edges thereof.

4. The orthodontic remodeling device of claim 1, wherein said metal core is a wire that is bent in a single plane in a back and forth pattern a plurality of times to form said U-shape outline.

5. The orthodontic remodeling device of claim 1, wherein said flexible biocompatible polymer comprises a silicone.

6. The orthodontic remodeling device of claim 1, wherein said extra-oral driver includes a water resistant housing containing a vibratory source operably coupled to a power source operably coupled to a processor for controlling device usage and for recording and transmitting usage compliance data.

7. The orthodontic remodeling device of claim 6, wherein said orthodontic remodeling device vibrates at 20-40 Hz and 0.1-0.3 Newtons.

8. An intra-oral orthodontic remodeling device comprising a vibrating bite plate, said bite plate comprising:
   i) a shapeable metal core that is substantially flat and U-shaped in outline to fit between occlusal surfaces of teeth;
   ii) a flexible biocompatible covering on said metal core;
   iii) said flexible biocompatible covering having an outside edge having upper and lower rims to contact an upper and lower facial surfaces of teeth;
   iv) said flexible biocompatible covering having an inside edge having optional upper and lower rims to contact at least a portion of an upper and lower lingual surfaces of teeth;
   v) wherein said metal core has a vibrator on a surface thereon operably coupled to a battery or charge capacitor and wherein said vibrator and battery or charged capacitor are hermetically sealed;
   vi) said shapeable metal core and flexible biocompatible covering allowing a bend such that a molar end of said bite plate can move at least one cm towards or away from a midline of said bite plate; and
   vii) wherein said intra-oral orthodontic remodeling device vibrates to accelerate orthodontic remodeling.

9. The intra-oral orthodontic remodeling device of claim 8, wherein said shapeable metal core is a planar piece of metal with a plurality of wedge cutouts in an edge thereof.

10. The intra-oral orthodontic remodeling device of claim 8, wherein said shapeable metal core is a wire.

11. The intra-oral orthodontic remodeling device of claim 8, wherein said shapeable metal core is a wire that travels back and forth a plurality of times in a planar path.

12. The intra-oral orthodontic remodeling device of claim 8, wherein said flexible biocompatible polymer comprises a silicone.

13. The intra-oral orthodontic remodeling device of claim 8, wherein said intra-oral orthodontic remodeling device vibrates at 20-40 Hz and 0.1-0.3 Newtons.

14. A method of orthodontic remodeling, comprising a patient wearing a fixed orthodontic appliance or an aligner biting the bite plate of the orthodontic remodeling device of claim 7, and applying vibration for about 10-20 minutes daily, wherein the orthodontic remodeling requires about half the time with the orthodontic remodeling device, as compared to the use of the fixed orthodontic appliance or the aligner alone.

15. A method of orthodontic remodeling, comprising a patient wearing a fixed orthodontic appliance or an aligner biting the bite plate of the orthodontic remodeling device of claim 13, and applying vibration for about 10-20 minutes daily, wherein the orthodontic remodeling requires about half the time with the orthodontic remodeling device, as compared to the use of the fixed orthodontic appliance or the aligner alone.

* * * * *